(12) United States Patent
Raab (10) Patent No.: US 6,984,236 B2
(45) Date of Patent: *Jan. 10, 2006

(54) BONE CONNECTIVE PROSTHESIS AND METHOD OF FORMING SAME

(75) Inventor: Simon Raab, Maitland, FL (US)

(73) Assignee: Faro Technologies, Inc., Lake Mary, FL (US)

(*) Notice: Subject to any disclaimer, the term of this patent is extended or adjusted under 35 U.S.C. 154(b) by 173 days.

This patent is subject to a terminal disclaimer.

(21) Appl. No.: 10/279,245

(22) Filed: Oct. 24, 2002

(65) Prior Publication Data

US 2003/0130736 A1 Jul. 10, 2003

Related U.S. Application Data

(60) Provisional application No. 60/335,961, filed on Oct. 24, 2001.

(51) Int. Cl.
*A61F 1/24* (2006.01)

(52) U.S. Cl. ............... 606/76; 427/2.26; 427/388.2; 427/388.5

(58) Field of Classification Search .............. 623/23.37, 623/23.36, 16.11
See application file for complete search history.

(56) References Cited

U.S. PATENT DOCUMENTS

| | | |
|---|---|---|
| 2,916,469 A | 12/1959 | Lai |
| 3,078,180 A | 2/1963 | Zander et al. |
| 3,197,340 A | 7/1965 | Bellinger |
| 3,351,504 A | 11/1967 | DeHart |
| 3,446,875 A | 5/1969 | Bruckmann et al. |
| 3,544,356 A | 12/1970 | Vazirani |

(Continued)

OTHER PUBLICATIONS

International Search Report PCT/US02/34139.
Wittington, "Wittington's Dictionary of Plastics", Technomic Publishing Co., Inc., 1978, pp. 287–288.
Bikales, N.M. Editor, Adhesion and Bonding, John Wiley and Sons, Inc., New York, 1971, pp. 45–46.
Ingwersen, O.S. et al., Editors, The Knee Joint, Excerpta Medica Amsterdam, American Elsevier Publishing Co., Inc., New York, 1974, Chapter Entitled "Mechanical Properties of Bone Cements In Vitro and Invivo", pp. 1–5.
"Ceramic Implants", Hench L.L., Director of Biomedical Engineering, University of Florida, Gainesville, Florida, 1975.
S. Sauberlich et al., "Cell culture tests for assessing the tolerance of soft tissue to variously modified titanium surfaces", Clinical Oral Implants Research 10 (5), 379–393.
"12. Dental Cements –2. Resin Cements" www..ucc.ie/ucc/depts/restorative/dentext/dchap12.pdf.
Yerby et al., "The effect of a saline coupling agent on the bond strength of bone cement and cobalt–chrome alloy", Journal of Biomedical Materials Research, vol. 49, Issue 1, 2000, pp. 127–133.

(Continued)

*Primary Examiner*—Cary E. O'Connor
*Assistant Examiner*—Candice C. Stokes
(74) *Attorney, Agent, or Firm*—Cantor Colburn LLP (57) ABSTRACT

The above-discussed and other problems and deficiencies of the prior art are overcome or alleviated by the improved bone connective prosthesis and method of forming the same of the present invention, comprising the addition of at least one biocompatible metal coupling agent to a prosthetic element, and then adding the biocompatible copolymerizer 2-hydroxyethyl methacrylate ("HEMA") to the PMMA film and/or cement in an amount effective to enhance the cohesion between the prosthetic and the bone cement. In general, a PMMA/HEMA film is applied to the prosthetic element in the presence of a silane coupling agent by dipping, painting, spraying, etc.

58 Claims, 2 Drawing Sheets

U.S. PATENT DOCUMENTS

| | | |
|---|---|---|
| 3,647,498 A | 3/1972 | Dougherty |
| 3,649,345 A | 3/1972 | Tolosa |
| 3,663,288 A | 5/1972 | Miller |
| 3,713,860 A | 1/1973 | Auskern |
| 3,790,507 A | 2/1974 | Hodosh |
| 3,907,609 A | 9/1975 | Coggins |
| 3,936,887 A | 2/1976 | Hodosh |
| 3,938,198 A | 2/1976 | Kahn et al. |
| 3,957,529 A | 5/1976 | Alexander et al. |
| 3,987,499 A | 10/1976 | Branemark et al. |
| 4,065,817 A | 1/1978 | Branemark et al. |
| 4,202,055 A | 5/1980 | Reiner et al. |
| 4,234,972 A | 11/1980 | Hench et al. |
| 4,268,639 A | 5/1981 | Seidel et al. |
| 4,336,618 A * | 6/1982 | Raab ............... 623/23.59 |
| 4,341,691 A | 7/1982 | Anuta |
| 4,365,359 A * | 12/1982 | Raab ............... 606/76 |
| 4,404,327 A | 9/1983 | Crugnola et al. |
| 4,536,158 A | 8/1985 | Bruins et al. |
| 4,645,456 A | 2/1987 | James |
| 4,648,845 A | 3/1987 | Orlowski et al. |
| 4,718,910 A | 1/1988 | Draenert |
| 4,719,149 A | 1/1988 | Aasen et al. |
| 4,837,279 A | 6/1989 | Arroyo |
| 4,880,660 A | 11/1989 | Aasen et al. |
| 4,937,144 A | 6/1990 | Podszun et al. |
| 5,147,903 A | 9/1992 | Podszun et al. |
| 5,258,420 A | 11/1993 | Posey-Dowty et al. |
| 5,264,513 A | 11/1993 | Ikemura et al. |
| 5,290,318 A | 3/1994 | Ling et al. |
| 5,480,450 A | 1/1996 | James et al. |
| 5,507,814 A | 4/1996 | Gilbert et al. |
| 5,525,648 A | 6/1996 | Aasen et al. |
| 5,534,562 A | 7/1996 | Jensen et al. |
| 5,702,485 A | 12/1997 | Burke et al. |
| 6,051,751 A | 4/2000 | Sioshansi et al. |
| 6,136,038 A * | 10/2000 | Raab ............... 623/23.37 |
| 6,203,844 B1 | 3/2001 | Park |
| 6,218,015 B1 | 4/2001 | Allen et al. |

OTHER PUBLICATIONS

K.P. Andriano et al., "Biocompatibility and Mechanical Properties of a Totally Absorbable Composite Material for Orthopaedic Fixation Devices", Journal of Applied Biomaterials, vol. 3, No. 3, Fall 1992, pp. 197–206.

A.F. Paal et al., "The Effect Of A Saline Bonding Agent At The Bone Cement–Implant Interface", 45th Annual Meeting, Orthopaedic Research Society, Feb. 1–4, 1999, Anaheim, Ca.

* cited by examiner

BONE CONNECTIVE PROSTHESIS AND METHOD OF FORMING SAME

CROSS REFERENCE TO RELATED APPLICATIONS

This application claims priority to U.S. Provisional Application Ser. No. 60/335,961, filed Oct. 24, 2001, the entire contents of which are specifically incorporated herein by reference.

BACKGROUND OF THE INVENTION

In the field of orthopedic surgery, ZIMALOY manufactured by Zimmer, U.S.A. Inc., a chromium-cobalt-molybdenum alloy, stainless steel, titanium alloys, and polymerized materials such as ultra high molecular weight polyethylene (hereinafter UHMWPE) have been used successfully to replace the ends of long bones and joints, including the hip joint. However, there exists a severe limitation with respect to such orthopedic surgery, namely, coupling of the prosthesis to bone. Due to such factors as mechanical stress, fatigue, corrosion, etc., the prosthesis/bone cement joints have been prone to failure.

Present methods of utilizing such bone prosthesis involve the use of a prosthesis having a stem portion which is inserted into the interior of a bone. A bone cement comprising a mixture of polymethylmethacrylate ("PMMA") polymer and methyl methacrylate monomer and optionally including a styrene copolymer of PMMA is likewise inserted into the bone cavity and utilized to couple the stem of the implant to the bone itself. Experience has demonstrated, however, that serious drawbacks exist with respect to the coupling between the prosthesis stem and the bone cement. Attempted solutions to this problem have been directed primarily toward strengthening the prosthesis/bone cement interface by means of gross mechanical interlock involving, for example, dove tails, small stems, and the like. Such devices result in stress concentrations that can exceed the strength of the bone cement and that can cause non-physiological force distribution in the bone.

Adherence at the interface between the implant and PMMA is greatly restricted by current industrial and surgical practices. For instance, the PMMA cement is typically applied in a highly viscous, doughy state with the result that the degree of contact between the implant and the cement is inadequate. Moreover, the existence of wear boundary layers such as contaminants and weak metal oxides on the surface of the implant have also caused problems. Weak boundary layers may be due to the composition of the implant or to the process of forming the same. Thus, in the case of a metal implant, the surface of the implant normally includes weak metal oxides as weak boundary layers. Finally, the implant may come in contact with air, blood or water prior to being inserted into the bone, thereby becoming contaminated. The existence of weak boundary layers, e.g., surface contaminants, is detrimental to the formation of good implant bone cement adherence. Thus, the strength of such joints has been dependent upon gross mechanical interlock. Such difficulties in the formation of a satisfactory prosthesis/bone cement connection have also made resurfacing of a deteriorated joint, e.g., a deteriorated hip joint due to arthritis, difficult to accomplish. Thus, in the case of a deteriorated articular surface, e.g., surface of the head or ball in a ball and socket joint, the entire head of the bone is generally removed and a prosthetic head is connected to the bone; although in some instances, resurfacing implants have been used with bone cement.

U.S. Pat. No. 4,336,618 to Simon Raab, which is assigned to the assignee hereof, all of the contents of which are incorporated herein by reference, taught that the aforementioned prosthesis fixation problems could be overcome by treating at least that portion of the prosthesis which is adapted to be connected to bone with a PMMA film fixedly adhered to said portions of the prosthesis. Prior to the application of the PMMA film, the surface to be coated is treated to prevent formation of a weak boundary layer upon bonding of a bone cement to an applied film. Thereafter, a PMMA film is applied by dipping, painting, spraying, etc., and finally, after the film has dried, it is annealed to remove any stresses in the film.

U.S. Pat. No. 6,136,038 to Simon Raab, which is assigned to the assignee hereof, all of the contents of which are incorporated by reference, improved upon U.S. Pat. No. 4,336,618, by lowering implant fixation failure rates, particularly those failures resulting from impact and shock conditions. U.S. Pat. No. 6,136,038 teaches that the combination of a biocompatible plasticizer with the PMMA film/cement helps to increase the resistance level of PMMA under high impact loading. The preferred plasticizer comprises the FDA approved, biocompatible hydrophilic monomer, 2-hydroxyethyl methacrylate ("HEMA").

According to U.S. Pat. No. 6,136,038, the resultant prosthesis has a film of PMMA/HEMA firmly adhered to the surface thereof. This PMMA/HEMA film adhesively interacts molecularly with PMMA and/or PMMA/HEMA bone cement. Accordingly, the adherence of a prosthesis adhesively connected to bone by means of a PMMA or PMMA/HEMA cement can be drastically increased.

To summarize the teachings of U.S. Pat. No. 4,336,618 and U.S. Pat. No. 6,136,038 discussed hereinabove, the PMMA/HEMA film is fixedly adhered to those portions of the prosthesis which are adapted to be connected to bone. Prior to the application of the PMMA/HEMA film, the surface to be coated is treated to prevent formation of a weak boundary layer upon bonding of a bone cement to an applied film. The methods used for the application of the precoats typically include preparing the metal surface by cleaning and passivation, and then either solvent based lacquer polymerizing solutions of monomer catalyst or inhibitor, and polymer electrostatically-applying or dip-applying power coatings. In all cases, some curing and/or annealing heat cycles are used. Thereafter, a PMMA/HEMA film is applied by dipping, painting, spraying, etc., and finally, after the film has dried, it is annealed to remove any stresses in the film. The overall composition of the coating has been limited to the PMMA/HEMA composition and other standard approved inhibitors and catalysts.

Current work in the field of prosthetics has focused on improving the bonding strength between the PMMA/HEMA treated prosthetic to bone. A recurring and predominant problem associated with prostheses is debonding at the implant-cement interface. Such debonding causes cracking around the implant and through the cement mantle to the bone. In addition to increasing bonding strength, pretreatment of the prosthetic element with an agent that can increase the durability of the prosthesis in a saline environment is also desirable. A deterrent to achieving both adhesiveness and durability is the limited number of biocompatible coupling agents capable of enhancing adhesion between the bone cement and the prostheses.

BRIEF DESCRIPTION OF THE INVENTION

The above-discussed and other problems and deficiencies of the prior art are overcome or alleviated by the improved bone connective prosthesis and method of forming the same of the present invention, comprising the addition of at least one biocompatible metal coupling agent to a prosthetic element, and then adding the biocompatible copolymerizer 2-hydroxyethyl methacrylate ("HEMA") to the PMMA film and/or cement in an amount effective to enhance the cohesion between the prosthetic and the bone cement. Preferably, this biocompatible metal coupling agent comprises a silane coupling agent, which may be applied by dipping, painting, spraying, etc.

In one embodiment of the present invention, a PMMA/HEMA film is applied to a prosthetic element in which the prosthetic element has been treated with a silane coupling agent. Alternatively, the silane coupling agent is mixed with the PMMA/HEMA film, and then applied in combination to the prosthetic element. In both embodiments, the resultant prosthesis has a film of PMMA/HEMA firmly adhered to the surface thereof. This PMMA/HEMA film adhesively interacts molecularly with PMMA or PMMA/HEMA bone cement. Accordingly, the adherence of a prosthesis adhesively connected to bone by means of a PMMA or PMMA/HEMA cement can be dramatically increased.

The above-discussed and other features and advantages of the present invention will be appreciated and understood by those of ordinary skill in the art from the following detailed discussion and drawings.

BRIEF DESCRIPTION OF THE DRAWINGS

Referring now to the drawings, wherein like elements are numbered alike in the several Figures.

DETAILED DESCRIPTION

According to the present invention, prostheses exhibiting marked fixation and durability improvements and methods for making the improvements have been discovered. Such a prosthesis comprises a prosthetic element having a PMMA/HEMA film fixedly adhered to at least a portion of the surface of the prosthetic element. The prosthesis includes a surface adapted to be fixedly attached to bone or a bone attachment surface. At least the bone attachment portion of the surface, in accordance with the present invention, is coated with a PMMA/HEMA film prior to attachment to bone. The PMMA/HEMA coating or film is adhered to the prosthetic element by a process which comprises applying PMMA/HEMA to the surface of a prosthetic element in the presence of a biocompatible and effective coupling agent, such as silane.

The rigid prosthetic element which is coated in accordance with the present invention may be chosen from any suitable biocompatible material including metal alloys and plastic. Thus, the element may be composed of a titanium alloy (e.g., Ti-6Al-4V), stainless steel (e.g., SS316LVM), or a cobalt-chromium or cobalt-chromium molybdenum alloy, MP-35 (protozol).

In order to provide a high strength PMMA/HEMA copolymer film in accordance with the present invention, the prosthetic element is first prepared. Preparation involves removal of any contaminants which may act as weak boundary layers so that the coating may be joined directly to the prosthetic element with no intervening material. In the case of a metal prosthetic element, the weak boundary layer may comprise contaminants such as dirts and oils, and additionally typically includes weak metal oxides.

In the case of a metal prosthetic element, the treatment to prevent the formation of a weak boundary layer upon bonding of the bone cement to an applied layer comprises degreasing followed by removal of the weak metal oxides by an acid treating step, which may be followed by a desmutting and passivation step. However, any treatment which functions effectively to remove contaminants and weak metal oxides may be utilized.

After preparing the prosthetic element, the PMMA/HEMA film, either in admixture with the biocompatible coupling agent, or after treatment of the surface of the prosthetic element with the biocompatible coupling agent, is prepared. Although the film comprises a PMMA/HEMA copolymer possibly in conjunction with a coupling agent, it is within the scope of this invention, that other materials known in the art may be included in the film, such as crosslinking agents, free radical catalysts, activators, other plasticizers, chain transfer agents, and inhibitors, as well as adhesion promoters in the form of co-polymers, such as of acrylic acid and other freely orienting polar molecules.

After preparation, the PMMA/HEMA film is applied to the prosthesis. The film may be applied by painting, spraying, dipping, powder coating, electrostatic coating, or in any suitable manner in the form of a lacquer, powder or emulsion. The method and form utilized will depend on a number of various factors including the desired coating thickness, strength, implant geometry and surface roughness.

Figure 1:
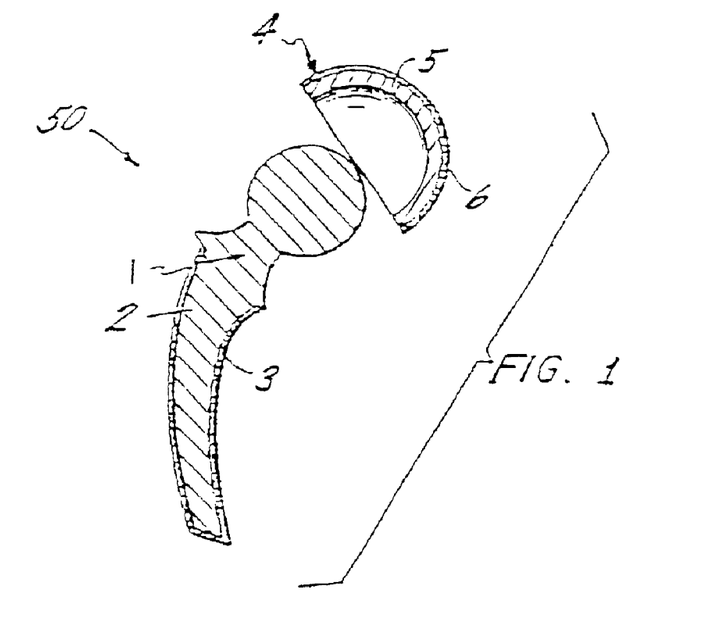
FIG. 1 is an elevational side view in longitudinal section of a PMMA and HEMA coated hip prosthesis prepared in accordance with the present invention.
Figure 2:
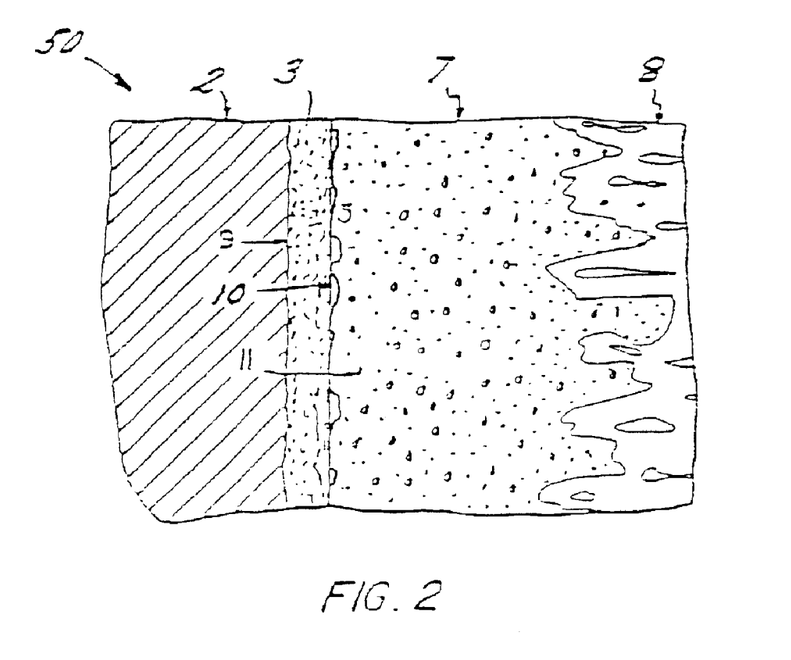
FIG. 2 is an enlarged fragmentary view of a PMMA and HEMA coated bone implant, as shown in FIG. 1, which has been fixedly adhered to the interior of a bone by means of a PMMA/HEMA bone cement.

In accordance with one embodiment of the present invention, an optimally plasticized prosthesis bound to coupling agents and exhibiting marked fixation improvements, along with marked resistance to fracture in the implant cement and interface areas under high impact loading, is shown by FIGS. 1 and 2 at 50. Such, prosthesis 1 comprises a prosthetic element 2 having a PMMA/HEMA copolymer film 3 fixedly adhered to at least a portion of the surface of the prosthetic element 2 which has been surface treated with a coupling agent. Also shown is a resurfacing prosthesis 4 for the socket portion of a ball and socket joint, comprising a rigid prosthetic element 5 and a PMMA/HEMA film 6 combined with a coupling agent.

One of the problems with finding suitable coupling agents in the field of biological implants is the very limited range of materials considered biocompatible and, at the same time, effective. Suitable biocompatible coupling agents include, but are not limited to, conventional silane, zirconate, and titanate coupling agents. Preferred silane agents include N-beta-(aminoethyl)-gamma-aminopropyltrimethoxy silane, gamma-aminopropyltriethoxy silane, bis(beta-hydroxyethyl)-gamma-aminopropyltriethoxy silane, beta- (3,4-epoxycyclohexyl)ethyltrimethoxy silane, gamma-glycidoxypropyltrimethoxy silane, gamma-methacryloxypropyltrimethoxy silane, sulfonylazidosilanes, vinyl trichlorosilane, vinyltriethoxysilane, and vinyl-tris(beta-methoxyethyl)silane, and phenyltrimethoxysilane. Suitable zirconate coatings include neopentyl(diallyl)oxytri(dioctyl)pyrophosphate zirconate and neopentyl(diallyl)oxytri(N-ethylenediamino)ethyl zirconate. Suitable titanate coatings include neopentyl(diallyl)oxytrineodecanoyl titanate, and neopentyl(diallyl)oxytri(dioctyl)phosphate titanate.

In an exemplary embodiment, the coupling agent is a silane coupling agent. Silane coupling agents are organo-functional silane monomers that possess a dual reactivity. This property permits groups at one end of the molecule to hydrolyze to form silanols (Si—OH) which are able to condense with similar groups on glass or with metal oxides. At the other end of the silane molecule are organic groups which are able to react with an organic resin. The reaction mechanism of the resin with the silane in the case of thermosetting resins is specific to a given resin. It is generally accepted that the organo-functional group reacts with the thermosetting resins during cure. However, polymethylmethacrylate is a thermoplastic resin so that the mechanisms suggested above do not necessarily apply since thermoplastics are pre-polymerized before actual use. Thermoplastic resins demonstrate relative chemical inertness. It is postulated that a chemical reaction takes place between the resin and the silane. This reaction can take several forms, namely, reaction with labile side groups or end groups on the polymer backbone, or reaction with polymer fragment radicals generated by chain scission of the polymer at molding temperature as well as by transesterification involving rupture of the polymer side chain.

After preparing the prosthetic element and the PMMA/HEMA film, the film is applied to the prosthesis. In one embodiment, the copolymer film is applied as a dry coat to the prosthetic element. The dry coat comprises a copolymer of PMMA/HEMA and is in the form of a film. The dry coat and in particular the HEMA component may be hydrated in a variety of ways to effectively plasticize the material.

A preferred method of applying the film to the prosthetic element comprises the application of a PMMA/HEMA lacquer to the element. Application may take the form of dipping, spraying, and the like. A PMMA/HEMA lacquer is prepared by dissolving PMMA/HEMA copolymer high molecular weight beads in a solvent such as dichloromethane. A small amount of barium sulfate may be added to the lacquer in order to keep the coated surface from crazing as well as making the coating radiopaque. The concentration of polymer in the solution should be in the range of 0.01 g per ml to about 0.8 g per ml, preferably from about 0.2 g per ml to about 0.4 g per ml, most preferably from about 0.25 g per ml to about 0.35 g per ml. The prosthetic element is immersed in the lacquer for a period of time sufficient to form a suitable coating on the surface of the element. Such a period of time may range from about 5 seconds to about 60 minutes, preferably from about 15 minutes to about 60 minutes, most preferably from about 25 to about 35 minutes.

Another method for applying the film to the prosthetic element comprises the application of PMMA/HEMA to the prosthetic element. In the case of metal prosthetics, the PMMA/HEMA film should be annealed by exposing the coated element to a temperature above that of the glass transition temperature of PMMA/HEMA, i.e. 70°–90° C., preferably 80° C. The curing or annealing treatment is necessary to insure complete co-polymerization and removal of any volatile components from the film. High pressures, i.e. greater than 100 psi may be applied to inhibit bubble formation. Moreover, by heating the film to a temperature above the glass transition temperature of PMMA/HEMA, any mechanical stresses in the film developed during the drying thereof will be eliminated.

The rate at which the coated element is cooled following the annealing treatment is preferably carefully controlled to insure that it preferably does not exceed about 1.5° C. per minute until the coated element reaches a temperature of about 80° C. This insures that only minimal stresses are formed in the film during cooling. If desired the film may be crosslinked by chemical and/or radiation techniques.

The thickness of the film thus produced is not of critical importance; however, the preferred minimum thickness of the film should be about 0.0001 inch, more preferably about 0.001 inch, most preferably about 0.002 inch. Upon completion of the annealing or curing of the PMMA/HEMA film, the coated prosthetic element is ready for use as a prosthesis. If the prosthesis is a bone implant prosthesis, the interior of the bone is removed and cleaned and a PMMA or PMMA/HEMA bone cement is applied to the interior of the bone. Thereafter, the implant portion of the prosthesis, coated in accordance with the present invention is inserted into the interior of the bone. If desired, the coating may be softened with a solvent such as methyl methacrylate monomer prior to insertion into the bone. This causes the PMMA/HEMA to swell and soften, thus allowing for greater mechanical and chemical interaction between the coating and the bone cement.

In FIG. 1, PMMA/HEMA copolymer film 3 is adhesively fixed to copolymer PMMA/HEMA film 6 when the surface treated prosthesis 1 is connected to resurfacing prosthesis 4.

In FIG. 2, an enlarged fragmentary view of a coated prostheses which has been fixedly adhered to bone by means of a PMMA/HEMA bone cement and a coupling agent is illustrated. Prosthetic element 2 is connected to bone cement 7 via the PMMA/HEMA 3 along with the coupling agent. Bone 8 is shown to be adhered to the bone cement. The interface 9 between the PMMA/HEMA film and the element is free of defects and any weak boundary layer due to the precoating treatment of the element. The interface 10 between the PMMA/HEMA coating and bone cement 7, represents both a chemical and mechanical adherence. Flaws 11 in the bone cement 7 are displaced away from the interface 9 due to the thickness of the film 3.

When a PMMA/HEMA coating is applied to a prosthetic element in accordance with the present invention, the resulting prosthesis may be joined to bone cement and will exhibit markedly superior adherence compared to that obtained by use of a prosthesis that has not been treated or coated with a coupling agent. Similarly, the use of a PMMA/HEMA bone cement in accordance with the present invention exhibits markedly superior adherence between the prosthesis and bone cement.

The effect of the improved adherence between the prosthesis and bone cement results not only in improved adhesion of bone implant prosthesis to the interior of a bone but moreover may eliminate in some cases the need for using an implant stem. Thus, stems have been used in prosthesis to implant a steel object securely into the bone. However, typically, the reason for the implant is a surface deterioration of the joint, for example, due to arthritis, but a mere resurfacing was not easily accomplished because of the fixation problems. Recent advances in the application of cement to bone involves the pressurization of cement deep into the pores of bones creating intimate interlock. The only problem remaining has been the attachment of a metal surface to the cement without a stem. Such problems may be solved utilizing the PMMA/HEMA coated prostheses of the present invention.

Additionally, it should be noted that the PMMA/HEMA coated prosthesis, according to the present invention, is especially suited to prosthesis subject to shock such as the "ball" position of a human femur as compared with the prior art.

Figure 3:
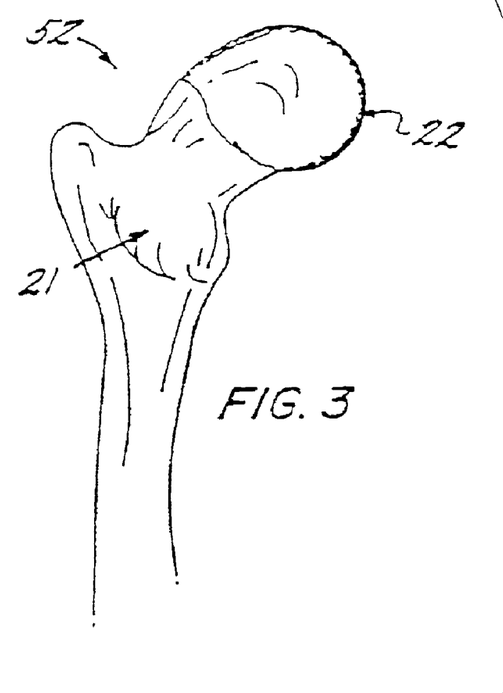
FIG. 3 is a side elevational view of a human femur having a deteriorated head surface.
Figure 4:
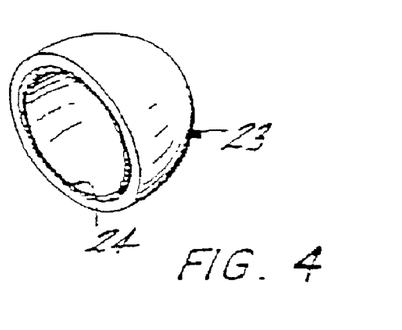
FIG. 4 is a perspective view of a prosthesis having a PMMA/HEMA coating on the bone connective surface thereof wherein the prosthesis may be utilized for resurfacing a deteriorated head surface of a ball and socket joint thus obviating the need for removal of the head portion of the joint.

Turning now to FIG. 3, there is shown a human femur 21 in elevational side view, with the head 52 thereof having a deteriorated surface 22, due for example, to arthritis or other known deterioration condition. Prior art would have preferred the removal of the entire head 52 of the femur and substitution of a complete prosthetic head connected to the femur by means of a stem insertion. However, by utilizing the present invention, a new exterior surface may be fixedly attached to the deteriorated surface 22 as can be seen in FIGS. 4 and 5.

Figure 5:
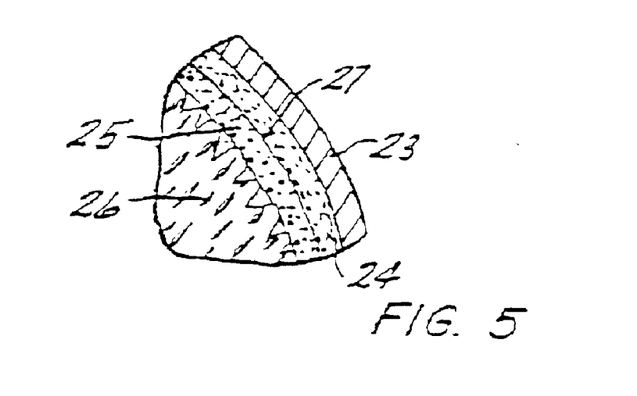
FIG. 5 is an enlarged fragmentary cross-section of a deteriorated femur head bearing the resurfacing prosthesis of FIG. 4.

FIG. 5 is an enlargement of a fragmentary cross-section of a femur head after resurfacing. Bone cement 25 is shown extending deeply into the surface of the bone 26. The bone cement 25 is connected to the PMMA/HEMA film 24 by molecular bonding at the PMMA/HEMA—PMMA/HEMA bone cement interface 27. The prosthetic element 23 is thus connected by means of the PMMA/HEMA film 24 and the bone cement 25 to the surface of bone 26. It is envisioned that resurfacing prosthesis of the present invention may be used not only for deteriorated ball and socket joints but may be used in general on any deteriorated articular surface including, for example, a deteriorated knee. It should be noted that the present invention is particularly useful when impact forces are required to be absorbed to assure long life of the implant.

The following methods, which embody the current invention, are shown by example, and are by no means to be limited by the example given.

EXAMPLES

Example 1

Preparation of a Prosthetic Element

Preparation of a metal prosthetic first begins by a degreasing process. The degreasing treatment may be carried out through the utilization of an aqueous alkaline solution, such as, for example, an aqueous solution of sodium hydroxide. Thus, the prosthetic element to be degreased may be immersed in a 1 N solution of sodium hydroxide which has been heated to its boiling point for 30 minutes to remove contaminants and grease. Another degreasing treatment which may be utilized with less contaminated elements comprises exposing the prosthetic element to trichloroethylene vapor. In order to determine whether or not degreasing is complete, the water break test may be utilized according to which the degreased prosthetic element is rinsed in distilled water. When the element is removed from the water, if the water beads up and runs off in less than 30 seconds, the surface is not clean enough. There should be no break in the film of water nor any tendency of the film to crawl or pucker.

Subsequent to the degreasing treatment, the metallic prosthetic element is preferably treated by acid etching in order to remove weakly bound metal oxides. Such treatment may comprise immersing the element in a sulfuric acid/water admixture at an elevated temperature of, for example, 60° C. for a period of approximately 30 minutes. Other treatments which may be used include immersing the prosthetic element in a sulfuric acid/sodium dichromate aqueous solution or treatment with other acid solutions.

It is preferred that acid etching be discontinued prior to any gross surface changes occurring. Thus, it is preferred that the surface which is designed to be attached to the bone be smooth. This results in a more continuous stress concentration about the prosthetic element/bone cement interface. However, where it is desired to use an implant having a rough surface, thus promoting a greater degree of mechanical interlock, the coating of the present invention may be utilized and a stronger joint will result.

In the case of an alloy prosthetic element which has been acid etched with the sulfuric acid solution discussed above, completion of the etching reaction is evidenced by the surface of the element turning black—this due to the presence of carbon which is a component of metal alloys. Such presence of carbon indicates that the surface has been sufficiently etched. If no carbon appears, then the etching is not complete. In order to avoid any gross surface changes, the element should be removed from the etching solution within ten seconds of the appearance of carbon. The etched element may be checked by means of a Hobsyn Tally Surface Profile or an SEM to insure that no gross surface changes have occurred.

Thereafter, any carbon remaining on the surface of the element is removed by means of a desmutting and passivation treatment. Such desmutting and passivation treatment may be carried out by means of a hydrofluoric acid/nitric acid aqueous admixture heated to an elevated temperature of approximately 60° C. Other strong oxidation reagents may be utilized if desired. When the etched element is immersed in such a solution, there should be a reaction within seconds as evidenced by a burst of bubbles as carbon is removed. This is followed by another sudden burst of bubbles evidencing a secondary reaction. At this point, the element should be removed from the desmutting and passivation solution. This treatment functions not only to remove carbon but additionally promotes the formation of a well adhered, uniform, high strength oxide surface, and is a preferred treatment step.

The initial removal of weak boundary layers may be carried out not only by chemical means, i.e. degreasing and acid etching, but also by mechanical means if desired. Thus, the prosthetic element may be treated by blasting with alumina grit to provide a virgin metal surface. Other mechanical treatments such as grinding, honing, machining, etc., may also be utilized.

Following mechanical treatment of the prosthetic element, the treated surface is immediately immersed in a passivation solution comprising, e.g. nitric and hydrofluoric acid, as above. It is preferred that the passivation treatment be carried out within a short time from the mechanical treatment. The lapse of time between mechanical treatment and passivation should be less than one minute.

Following passivation, the treated element should be rinsed in water until the water has a neutral pH. When the prosthetic element is composed of a Co—Cr—Mo alloy it is preferred that it be ultrasonically agitated while being rinsed. This removes weakly bound carbide particles which have been exposed in the etching process. These carbides reside naturally in cast or wrought Co—Cr—Mo alloys. The treated element should thereafter be dried by any suitable means such as by heating in an oven or by blowing the surface dry with a warm air stream.

Once the element has dried, it is allowed to cool to less than 30° C., e.g., to room temperature, prior to the application of the biocompatible coupling agent and the PMMA/HEMA film thereto. Care should be taken that the clean surface not be contaminated during drying or cooling. In the case of prosthetic elements composed of Ti-6Al-4V or Co—Cr—Mo alloys, and where silane is used as the coupling agent, the prosthetic element should be given a final treatment in an alkaline bath, e.g., in a 1 N NaOH solution at 96° C. for 30 minutes, prior to application of the silane coupling agent and the PMMA/HEMA film, and then cooled. Without the final alkaline bath just before application of the silane, the silane does not appear to bond to either the titanium or cobalt alloys.

Example 2

Coating the Prosthetic Element with a Silane Coupling Agent

The prosthetic element may be treated with the silane coupling agent before application of the PMMA/HEMA film. When used to treat the surface of a prosthetic element, the silane coupling agent is preferably in an aqueous solution comprising about 0.1 to about 1.0 percent by weight of the silane coupling agent; and the silane coupling agent is preferably prehydrolyzed, e.g., by the addition of an acid such as acetic acid.

In a preferred embodiment, the metal prosthetic is surface treated with a silane coupling agent. Here, the prosthetic element is degreased by washing three times with methylene chloride and dried for 30 minutes at 60° C. The prosthetic element is then soaked in 10% nitric acid for 45 minutes to passivate the surface, rinsed with deionized water, and dried for at least 1 hour at 60° C. The prosthetic element is then soaked for 5 minutes in a solution comprised of 5 volumes % of 3-(trimethoxysilyl)propyl methacrylate and 95 volume % ethanol. The prosthetic element is then removed from the solution, and dried at 90° C. under vacuum, and rinsed again with ethanol thereby removing any unbound silane. The resulting prosthetic element then contains the silane agent covalently attached to the steel with a group that will polymerize with the PMMA/HEMA coating. All of the silane is bound to the prosthetic element, thus there is no low molecular weight material present that would pose any toxicity risk.

Example 3

Preparation of a PMMA/HEMA/Silane Mixture Prior to Application to a Prosthetic Element When admixed with the PMMA/HEMA coating composition, the silane coupling agent is preferably used in an amount of about 0.01 to about 1.0 weight percent based on the weight of the PMMA/HEMA. When used in admixture with the PMMA/HEMA coating, it is preferred to wipe the surface of the prosthetic element with an alcohol, e.g., a mixture comprising 15% ethanol and 85% methanol after the coating procedure is finished in order to remove excess silane which diffuses to the coating surface where it may inhibit bone cement/coating interaction.

The weight ratio of PMMA and HEMA in the copolymer bonding film is not critical; however, the portion of HEMA should suitably be in the range between 2 weight % and 99 weight %. Preferably, the HEMA is present in an amount effective to provide enhanced adhesion and plasticization without adversely affecting the strength and other advantageous properties of the copolymer film.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A prosthesis comprising:
   a prosthetic element having a surface; and
   a hydrated polymethylmethacrylate 2-hydroxyethyl methacrylate copolymer film having an amount of 2-hydroxethyl methacrylate effective to improve elongation and having a first and second side, the first side disposed on at least a portion of the surface of the prosthetic element, the second side forming a bonding surface; and
   a metal coupling agent.

2. The prosthesis of claim 1, wherein the metal coupling agent is present either on the surface of the prosthetic element, or in combination with the polymethylmethacrylate 2-hydroxyethyl methacrylate copolymer film.

3. The prosthesis of claim 2, wherein the metal coupling agent comprises a silane, zirconate, or titanate coupling agent.

4. The prosthesis of claim 2, wherein the metal coupling agent comprises a silane coupling agent.

5. The prosthesis of claim 4, wherein the bonding surface is adapted to be fixedly attached to a bone by a bone cement.

6. The prosthesis of claim 4, wherein the prosthetic element surface is treated to prevent formation of a weak boundary layer upon bonding of the copolymer film to the prosthetic element surface.

7. The prosthesis of claim 6, wherein the prosthetic element comprises metal.

8. The prosthesis of claim 7, wherein the treatment to prevent the formation of a weak boundary layer comprises degreasing the metal prosthetic element and thereafter acid etching the prosthetic element.

9. The prosthesis of claim 6, wherein the prosthetic element comprises a cobalt-chromium-molybdenum alloy, stainless steel, or titanium alloy.

10. The prosthesis of claim 8, wherein the acid-etched prosthetic element surface is desmutted and passivated by treating the prosthetic element surface with an aqueous solution of hydrofluouric acid and nitric acid.

11. The prosthesis of claim 4, wherein the silane coupling agent is in combination with the polymethylmethacrylate 2-hydroxethyl methacrylate copolymer, the hydrated application of the polymethylmethacrylate 2-hydroxyethyl methacrylate copolymer film to the treated surface comprises providing a solution of hydrated polymethylmethacrylate 2-hydroxyethylmethacrylate and silane coupling agent, and applying the solution to the treated surface.

12. The prosthesis of claim 4, wherein the silane coupling agent is present on the surface of the prosthetic element, the hydrated application of the polymethylmethacrylate 2-hydroxyethyl methacrylate copolymer film to the treated surface comprises providing a solution of hydrated polymethylmethacrylate 2-hydroxyethylmethacrylate and applying the solution to the treated surface.

13. The prosthesis of claim 5, wherein the prosthesis is a bone implant.

14. The prosthesis of claim 5, wherein the prosthesis being adapted to be fixedly attached to an articular surface of a bone.

15. The prosthesis of claim 14, wherein the articular surface of the bone comprises the ball portion of a ball and socket joint.

16. The prosthesis of claim 5, wherein the hydrated polymethylmethacrylate 2-hydroxyethylmethacrylate copolymer film has a thickness greater than about 0.0001 inch.

17. The prosthesis of claim 5, wherein the prosthesis is fixedly adhered to a bone by bone cement comprising hydrated polymethylmethacrylate 2-hydroxyethyl methacrylate copolymer.

18. A prosthesis comprising:
a prosthetic element having surface; and
a hydrated methylmethacrylate 2-hydroxyethyl methacrylate copolymer film having an amount of 2-hydroxethylmethacrylate effective to improve elongation and having a first and second side, the first side disposed on at least a portion of the surface of the prosthetic element, the second side forming a bonding surface, wherein the bonding surface is adapted to be fixedly attached to a bone by a bone cement comprising a hydrated polymethylmethacrylate 2-hydroxyethyl methacrylate copolymer; and
a metal coupling agent.

19. The prosthesis of claim 18, wherein the metal coupling agent comprises a silane, zirconate, or titanate coupling agent.

20. The prosthesis of claim 18, wherein the metal coupling agent comprises a silane coupling agent.

21. The prosthesis of claim 20, wherein the prosthetic element surface is treated to prevent formation of a weak boundary layer upon bonding of the copolymer film to the prosthetic element surface.

22. The prosthesis of claim 21, wherein the prosthetic element comprises metal.

23. The prosthesis of claim 22, wherein the treatment to prevent the formation of a weak boundary layer comprises degreasing the metal prosthetic element with an alkaline reagent and thereafter acid etching the prosthetic element.

24. The prosthesis of claim 21, wherein the metal prosthetic element comprises a cobalt-chromium-molybdenum alloy, stainless steel, or a titanium alloy.

25. The prosthesis of claim 23, wherein the acid-etched prosthetic element surface is desmutted and passivated by treating the prosthetic element surface with an aqueous solution of hydrofluoric acid and nitric acid.

26. The prosthesis of claim 21, wherein the application of the polymethylmethacrylate 2-hydroxyethyl methacrylate copolymer film to the treated surface comprises providing a solution of hydrated polymethylmethacrylate 2-hydroxyethyl methacrylate and applying the solution to the treated surface.

27. The prosthesis of claim 20, wherein the prosthesis is a bone implant.

28. The prosthesis of claim 20, wherein the prosthesis being adapted to be fixedly attached to an articular surface of a bone.

29. The prosthesis of claim 28, wherein the articular surface of the bone comprises the ball portion of a ball and socket joint.

30. The prosthesis of claim 20, wherein the hydrated polymethylmethacrylate 2-hydroxyethyl methacrylate copolymer film has a thickness greater than about 0.0001 inch.

31. A process for preparing an improved prosthesis comprising a prosthetic element having a surface, the prosthesis adapted to be joined to bone by a bone cement which comprises:
treating the prosthetic element surface to prevent formation of a weak boundary layer upon bonding of the bond cement to an applied film;
applying a metal coupling agent to the prosthetic element surface;
applying a polymethylmethacrylate 2-hydroxyethyl methacrylate copolymer film having an amount of 2-hydroxethyl methacrylate effective to improve elongation to the treated surface;
annealing the polymethylmethacrylate 2-hydroxyethyl methacrylate copolymer film; and
hydrating the polymethylmethacrylate 2-hydroxethyl methacrylate copolymer film to form a hydrated polymethylmethacrylate 2-hydroxyethyl methacrylate copolymer film.

32. The method of claim 31, wherein the metal coupling agent comprises a silane, zirconate, or titanate coupling agent.

33. The method of claim 31, wherein the metal coupling agent comprises a silane coupling agent.

34. A process in accordance with claim 33, wherein the prosthetic element comprises metal.

35. A process in accordance with claim 34, wherein the treatment to prevent formation of a weak boundary layer upon bonding of the bonding cement to an applied film comprises degreasing the metal prosthetic element with an alkaline reagent and thereafter acid etching the prosthetic element.

36. A process in accordance with claim 34, wherein the metal prosthetic element comprises a cobalt-chromium-molybdenum alloy, a titanium alloy, or stainless steel.

37. A process in accordance with claim 35, wherein the prosthetic element surface is desmutted and passivated by treating the prosthetic element with an aqueous solution of hydrofluoric acid and nitric acid.

38. The process of claim 33, wherein the prosthesis is a bone implant.

39. The process of claim 33, wherein the prosthesis being adapted to be fixedly attached to an articular surface of a bone.

40. The process of claim 39, wherein the articular surface of the bone comprises the ball portion of a ball and socket joint.

41. The process of claim 33, wherein the hydrated polymethylmethacrylate 2-hydroxyethyl methacrylate copolymer film has a thickness greater than about 0.0001 inch.

42. The process of claim 33, wherein the film is hydrated by exposing the annealed film to an aqueous solution.

43. The process of claim 34, wherein said aqueous solution is a saline solution.

44. The process of claim 34, wherein said exposing is by packaging the prosthesis in said aqueous solution.

45. A process for preparing an improved prosthesis comprising a prosthetic element having a surface, the prosthesis adapted to be joined to bone by a bone cement which comprises:
treating the prosthetic element surface to prevent formation of a weak boundary layer upon bonding of the bond cement to an applied film;
applying a polymethylmethacrylate 2-hydroxyethyl methacrylate copolymer film combined with a metal coupling agent, wherein the film has an amount of 2-hydroxethyl methacrylate effective to improve elongation to the treated surface;
annealing the polymethylmethacrylate 2-hydroxyethyl methacrylate copolymer film; and
hydrating the polymethylmethacrylate 2-hydroxethyl methacrylate copolymer film to form a hydrated polymethylmethacrylate 2-hydroxyethyl methacrylate copolymer film.

46. The method of claim 45, wherein the metal coupling agent comprises a silane, zirconate, or titanate coupling agent.

47. The method of claim 45, wherein the metal coupling agent comprises a silane coupling agent.

48. A process in accordance with claim 47, wherein the prosthetic element comprises metal.

49. A process in accordance with claim 48, wherein the treatment to prevent formation of a weak boundary layer upon bonding of the bonding cement to an applied film comprises degreasing the metal prosthetic element with an alkaline reagent and thereafter acid etching the prosthetic element.

50. A process in accordance with claim 48, wherein the metal prosthetic element comprises a cobalt-chromium-molybdenum alloy, a titanium alloy, or stainless steel.

51. A process in accordance with claim 49, wherein the prosthetic element surface is desmutted and passivated by treating the prosthetic element with an aqueous solution of hydrofluoric acid and nitric acid.

52. The process of claim 47, wherein the prosthesis is a bone implant.

53. The process of claim 47, wherein the prosthesis being adapted to be fixedly attached to an articular surface of a bone.

54. The process of claim 53, wherein the articular surface of the bone comprises the ball portion of a ball and socket joint.

55. The process of claim 47, wherein the hydrated polymethylmethacrylate 2-hydroxyethyl methacrylate copolymer film has a thickness greater than about 0.0001 inch.

56. The process of claim 47, wherein the film is hydrated by exposing the annealed film to an aqueous solution.

57. The process of claim 56, wherein said aqueous solution is a saline solution.

58. The process of claim 56, wherein said exposing is by packaging the prosthesis in said aqueous solution.

* * * * *